US00PP31339P3

(12) United States Plant Patent
Delabroye

(10) Patent No.: US PP31,339 P3
(45) Date of Patent: Jan. 7, 2020

(54) ***SCHIZACHYRIUM* PLANT NAMED 'CHAMELEON'**

(50) Latin Name: *Schizachyrium scoparium*
Varietal Denomination: Chameleon

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 16/350,269

(22) Filed: Oct. 24, 2018

(65) Prior Publication Data

US 2019/0124814 P1 Apr. 25, 2019

(30) Foreign Application Priority Data

Oct. 24, 2017 (QZ) ..... PBR 20172688

(51) Int. Cl.
*A01H 5/12* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 6/46; A01H 5/12; A01H 5/02
See application file for complete search history.

*Primary Examiner* — Keith O. Robinson
(74) *Attorney, Agent, or Firm* — Penny J. Aguirre

(57) ABSTRACT

A new cultivar of *Schizachyrium scoparium*, 'Chameleon', that is characterized by its leaves that are striped green and cream in color in spring and early summer, its leaves that become flushed with pink and light purple in color in late summer and fall, and its small plant size.

2 Drawing Sheets

Botanical classification: *Schizachyrium scoparium.*
Varietal denomination: 'Chameleon'.

BACKGROUND OF THE INVENTION

The present invention relates to a new and distinct cultivar of *Schizachyrium scoparium* and will be referred to hereafter by its cultivar name, 'Chameleon'. 'Chameleon' represents a new cultivar of little bluestem, an ornamental grass grown for landscape use.

The new cultivar was discovered as a chance seedling by the Inventor in Hantay, France in May of 2014 in a trial field that had been planted with seeds of *Schizachyrium scoparium* 'The Blues' (not patented). The male parent of 'Chameleon' is therefore unknown.

Asexual propagation of the new cultivar was first accomplished under the direction of the Inventor by culm division in Rijswijk, The Netherlands in 2017. Asexual propagation of the new cultivar by culm division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Chameleon' as a new and unique cultivar of *Schizachyrium scoparium.*

1. 'Chameleon' exhibits leaves that are striped green and cream in color in spring and early summer.
2. 'Chameleon' exhibits leaves that become flushed with pink and light purple in color in late summer and fall.
3. 'Chameleon' exhibits a small plant size.

The female parent plant of 'Chameleon', 'The Blues', differs from 'Chameleon' in having foliage that is blue-green in color and in having a taller plant height. 'Chameleon' can be most closely compared to *Schizachyrium* cultivars 'MinnblueA' (U.S. Plant Pat. No. 17,310) and 'Cairo' (not patented). 'MinnblueA' differs from 'Chameleon' in having a taller plant height and foliage colors that are blue-green and fade to purple in the fall. 'Cairo' differs from 'Chameleon' in having a taller plant height and foliage colors that are olive green to bluish red.

BRIEF DESCRIPTION OF THE DRAWINGS

The accompanying colored photograph illustrates the overall appearance and distinct characteristics of the new *Schizachyrium*. The photograph was taken of 6-month-old plants as grown outdoors in 17-cm containers in Hantay, France.

The photograph in FIG. 1 provides a side view of the plant of 'Chameleon' in bloom.

Figure 1:
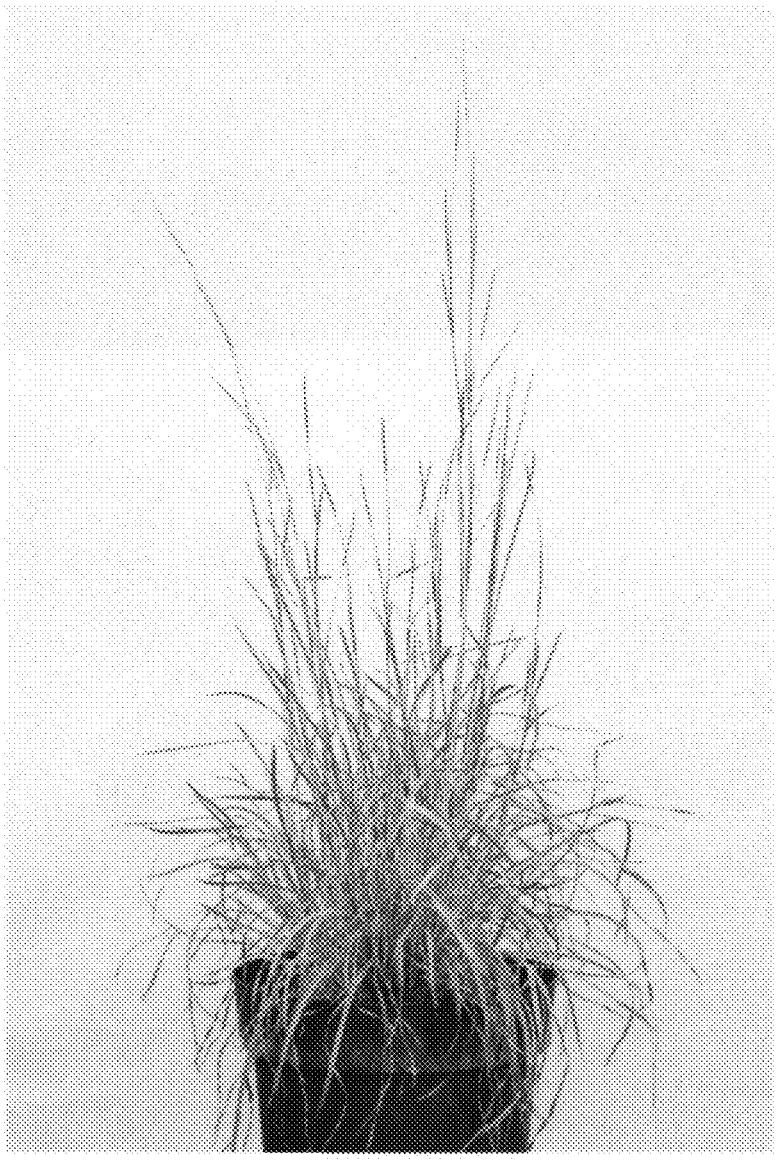
Figure 2:
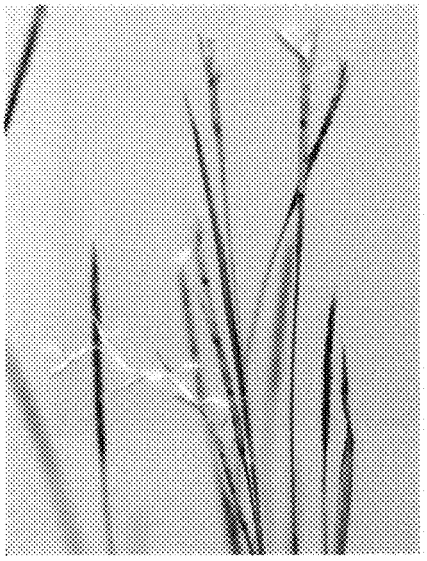

The photograph in FIG. 2 provides a close up of the inflorescence of 'Chameleon'.

Figure 3:
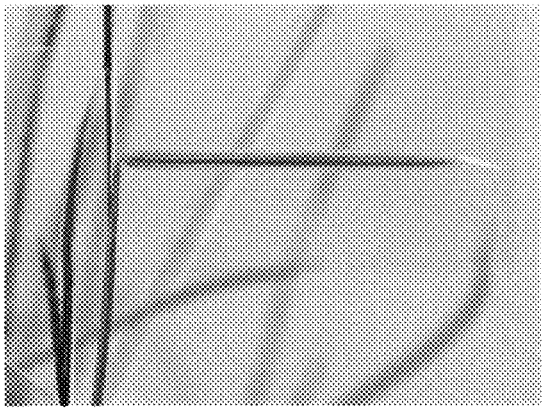

The photograph in FIG. 3 provides a close up of the foliage of 'Chameleon'.

Figure 4:
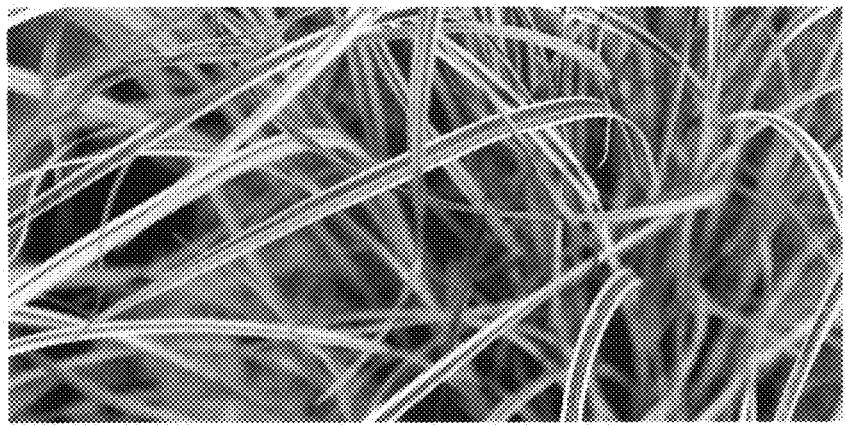

The photograph in FIG. 4 provides a close up of the foliage color in the fall of 'Chameleon'.

The colors in the photograph are as close as possible with the digital photography techniques available, the color values cited in the detailed botanical description accurately describe the colors of the new *Schizachyrium.*

DETAILED BOTANICAL DESCRIPTION

The following is a detailed description of 6-month-old plants of the new cultivar as grown outdoors in 17-cm containers in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—September to November in Hantay, France.

*Plant type*.—Herbaceous, perennial grass.

*Plant habit*.—Upright, ovate, small statured.

*Height and spread*.—Average of 38.2 cm in height from soil level to top of foliar plane, 58.5 cm in height from soil level to top of floral plane, average of 34.3 cm in diameter as grown in a 17-cm container.

*Hardiness*.—At least in U.S.D.A. Zones 3 to 9.

*Diseases and pests*.—No unique susceptibility/resistance to pests or diseases has been observed.

*Root description*.—Fibrous roots on woody rootstalks, 158D in color.

*Propagation*.—Culm division and tissue culture.

*Root development*.—An average of 6 weeks or root initiation and an average of 6 weeks to produce a young plant.

*Growth rate*.—Slow to moderate.

Culm (stem) description:

*Primary shoots*.—Average of 25.1 cm in length, 1 mm in diameter, internode 5.6 cm in length.

*Stem appearance and shape*.—Rounded to moderately angled (average; 2 angles).

*Stem luster*.—Slightly glossy.

*Stem aspect*.—Average of 5° from vertical.

*Stem strength*.—Strong.

*Stem color*.—Young; 150D, mature; 178A to 178B, covered by a thin waxy layer that is a color between 122D and 202D, fading to the base to become 152A and 145B, internodes 146A.

Foliage description:

*Leaf shape*.—Linear, sheathed with a leaf blade extending from ligule at nodes.

*Leaf division*.—Simple, margins entire.

*Leaf arrangement*.—Alternate.

*Leaf base*.—Sheathed to base of the node.

*Leaf apex*.—Narrow and long acuminate.

*Leaf venation*.—Parallel, not distinguishable in color from leaf, only main vein is visible.

*Leaf size*.—Average of 15.2 cm in length and 3 mm in width.

*Leaf aspect*.—Flat, slightly twisted.

*Leaf quantity*.—Average of 5 per shoot.

*Leaf surface*.—Both surfaces smooth, glabrous, matte.

*Ligule*.—Membranous, an average length of 1 mm and NN155A in color.

*Leaf color*.—Sheathing; 138B, margined 155D to 158D, fading to 180D at the base, young leaf upper surface; 137B, margined and axially striped NN155D, young leaf lower surface; between 136C and 137C, margined and axially striped NN155C, mature leaf upper surface between 136A and NN137A, margined and axially striped between 4D and 155D, vein 146B, mature leaf lower surface; 189A, margined and axially striped between 4D and 155D, vein 146B, autumn leaf color upper surface between 136A and NN137A, margined and axially striped 182A and 186B to 186C, autumn leaf color lower surface slightly lighter than N186A margined and axially striped 187C and 187D and lighter.

Flower description:

*Inflorescence*.—Spike, spikelets in pairs, consisting of 1 sterile spikelet and 1 fertile spikelet, average of 4.4 cm in height, 1 cm in diameter.

*Flower quantity*.—An average of 20 per inflorescence and 500 per plant.

*Time to flower*.—Average of 10 months.

*Flower buds*.—Average of 1.4 cm in length, 1 mm in diameter, linear in shape, smooth, glabrous and slightly glossy surface, colors; 182B, base tinged 147A.

*Flower description*.—Spikelets in pairs consisting of 1 sterile spikelet and 1 fertile spikelet, sterile spikelet consisting of a single glume, fertile spikelet consisting of 2 glumes and 2 lemmas.

*Flower aspect*.—Upright.

*Flowering habit*.—Moderate.

*Fragrance*.—None.

*Flower shape*.—Spikelets in pairs, consisting of 1 sterile spikelet, 1 fertile spikelet, typical for *Schizachyrium*.

*Flower size*.—Average of 1.5 mm in height and diameter, 1.5 cm in length.

*Flower longevity*.—Average of 1 month, persistent.

*Peduncles*.—An average of 8.8 cm in length, 3.5 mm in diameter, moderately strong, held vertical, smooth and glabrous, slightly glossy, 183D in color.

*Pedicel*.—Sterile spikelets pedicellate, fertile spikelets sessile, average of 1 mm in length, 0.5 mm in diameter, held in an average of 5° to axis, moderately strong, smooth, glabrous and matte surface, 201A in color.

*Spikelets*.—Sterile spikelets; consist of a single glume, linear in shape, average of 7 mm in length, 1 mm in width, apex narrow acute in shape, cuneate base, ciliate margins, both sides 201A to 201B in color, fertile spikelets; consist of 2 glumes and 2 lemmas, 1 lemma elongated with an awn, glumes and lemmas glabrous and very slightly glossy, 2 glumes oppositely placed at the base of each spikelet, lemmas oppositely placed above the glumes.

*Glumes*.—Flat to slightly concave, linear in shape, average of 5 mm in length, average of 1 mm in width, apex narrow acute in shape, cuneate base, immature and mature upper and lower surface colors N200C to N200D, tinged N77C, no venation visible on glumes.

*Lemmas*.—Concave to linear in shape, average length of shortest lemma is 7 mm, average length of longest lemma with awn is 1.3 cm, average width of both lemmas is 0.75 cm, top shortest lemma is narrow and acute in shape, top of longest lemma is pungent and awn-like, base of both lemmas is cuneate, colors of immature and mature lemmas are similar; upper side of shortest lemma is N200D, slightly tinged N77C, towards the top tinged 147C, lower side of the shortest lemma is N200C, tinged N77C, margined 147B, both surfaces of longest lemma 155D, lower half margined N77C, no venation visible on lemmas.

Reproductive organs:

*Androecium*.—No stamens present.

*Gynoecium*.—Pistil; 2, average of 1 mm in length, 2 plumose stigmas on short, file styles, stigma; color is 200C, 0.75 mm in length and 0.5 mm in width, style; an average of 0.25 mm in length, 200C in color, ovary; 200C in color.

*Seeds*.—None observed to date.

It is claimed:

1. A new and distinct cultivar of *Schizachyrium* plant named 'Chameleon' as herein illustrated and described.

* * * * *